(12) United States Patent
Springman

(10) Patent No.: US 8,523,833 B2
(45) Date of Patent: Sep. 3, 2013

(54) SANITARY NAPKIN

(76) Inventor: Barbara A. Springman, North Ridgeville, OH (US)

( * ) Notice: Subject to any disclaimer, the term of this patent is extended or adjusted under 35 U.S.C. 154(b) by 537 days.

(21) Appl. No.: 12/662,551

(22) Filed: Apr. 22, 2010

(65) Prior Publication Data

US 2010/0305538 A1     Dec. 2, 2010

Related U.S. Application Data

(60) Provisional application No. 61/213,292, filed on May 27, 2009.

(51) Int. Cl.
   *A61F 13/15*          (2006.01)
   *A61F 13/20*          (2006.01)

(52) U.S. Cl.
   USPC ............. 604/385.01; 604/385.17; 604/385.18

(58) Field of Classification Search
   USPC .................. 604/385.17, 385.18, 358, 904
See application file for complete search history.

(56) References Cited

U.S. PATENT DOCUMENTS

| | | | |
|---|---|---|---|
| 4,627,848 A * | 12/1986 | Lassen et al. | ................. 604/370 |
| 6,913,573 B1 | 7/2005 | Viscomi et al. | |
| 2002/0082580 A1 | 6/2002 | Bennett | |
| 2004/0167479 A1 | 8/2004 | Warren et al. | |
| 2008/0097366 A1* | 4/2008 | Mathews | ................. 604/385.18 |

FOREIGN PATENT DOCUMENTS

WO    WO 2008033846 A2 *   3/2008

* cited by examiner

*Primary Examiner* — Elizabeth Houston
*Assistant Examiner* — Aundria Hairell
(74) *Attorney, Agent, or Firm* — Richard C. Litman

(57) ABSTRACT

The sanitary napkin includes an inner core of absorbent material that is spirally or helically wound along its length and tapers in diameter from a larger first end to a smaller second end. A layer of soft, pliable, liquid-pervious material encapsulates the inner core. The larger end of the napkin is configured in a thin flat profile and is provided a string or other positioning member to enhance placement and removal of the napkin. Although described above as an absorbent pad for vaginal discharge, it is recognized that the napkin could also be used to absorb rectal discharge in instances after hemorrhoid surgery and the like.

4 Claims, 3 Drawing Sheets

SANITARY NAPKIN

CROSS-REFERENCE TO RELATED APPLICATION

This application claims the benefit of U.S. Provisional Patent Application Ser. No. 61/213,292, filed May 27, 2009.

BACKGROUND OF THE INVENTION

1. Field of the Invention

The present invention generally relates to personal hygiene devices, and particularly to a sanitary napkin that provides an absorbent pad adapted to prevent leakage due to vaginal or other discharges.

2. Description of the Related Art

The problems of absorbing menses during the menstrual cycle are well known. The leakage of such menses can occur at any time, but is especially prevalent when one lies down for the evening or to take a quick nap. At such times the fluid tends to run between the buttocks and onto undergarments, nightclothes and bed linens causing stains thereto. Aside from the psychological angst produced by such staining, extra effort is required to clean the affected objects. There are a plethora of hygiene-related products available in the market place for preventing leakage of menses. However, the market place will always welcome a more effective device for solving these vexing problems. Thus, a sanitary napkin solving the aforementioned problems is desired.

SUMMARY OF THE INVENTION

The sanitary napkin of the present invention includes an inner core of absorbent material that is spirally or helically wound along its length and tapers in diameter from a larger first end to a smaller second end. A layer of soft, pliable, liquid-pervious material encapsulates the inner core. The larger end of napkin is configured in a thin flat profile and is provided a string or other positioning member to enhance placement and removal of the napkin. Although described above as an absorbent pad for vaginal discharge, it is recognized that the napkin could also be used to absorb rectal discharge in instances after hemorrhoid surgery and the like.

Accordingly, the invention presents an improved sanitary napkin having a substantially cylindrical configuration. The napkin prevents or substantially diminishes the chances of fluid leakage. The napkin is easy to use and is provided with an aid to enhance placement and removal. The invention provides for improved elements thereof in an arrangement for the purposes described that are inexpensive, dependable and fully effective in accomplishing their intended purposes.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
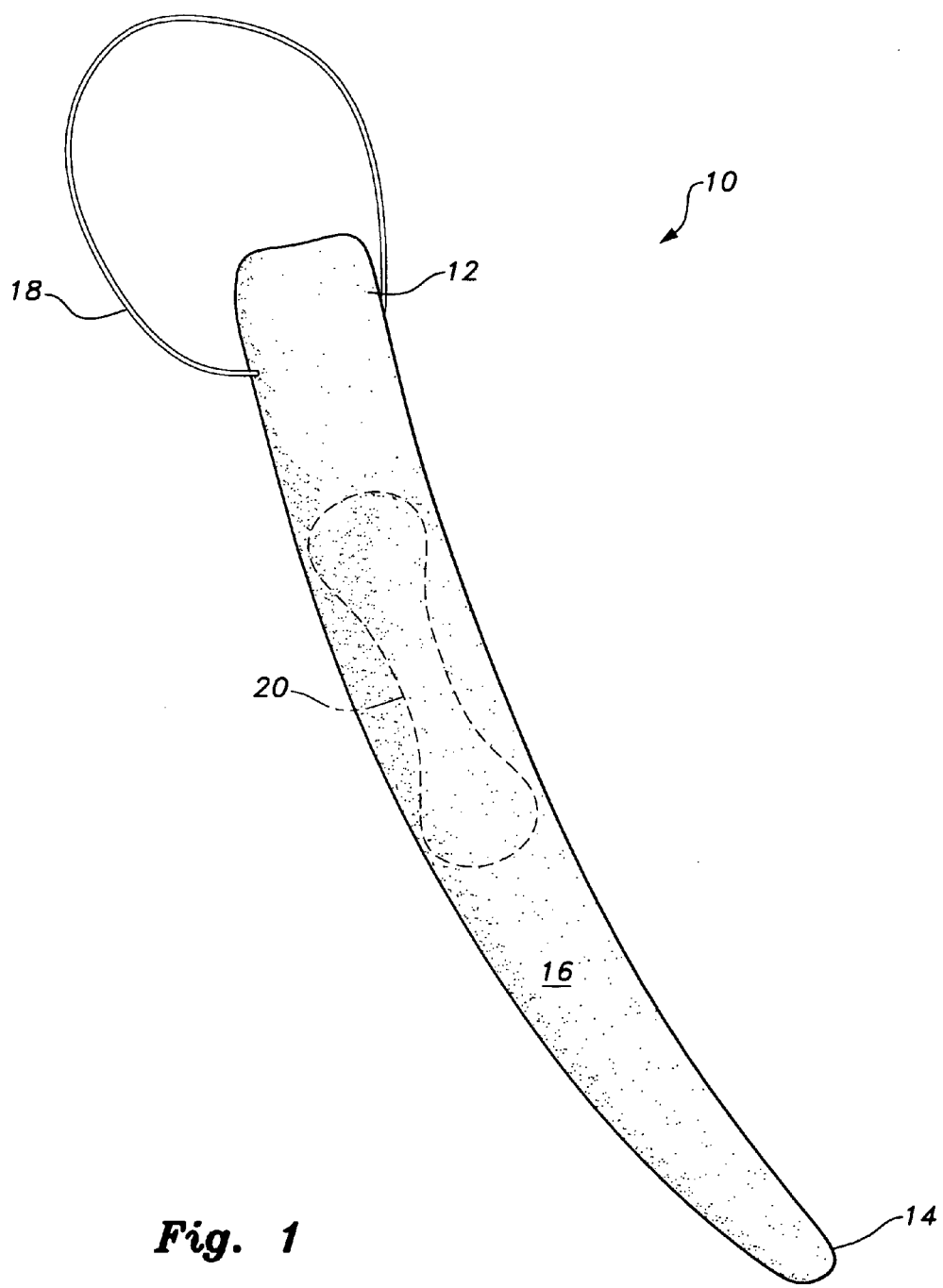
FIG. 1 is a perspective view of a sanitary napkin according to the present invention.
Figure 2:
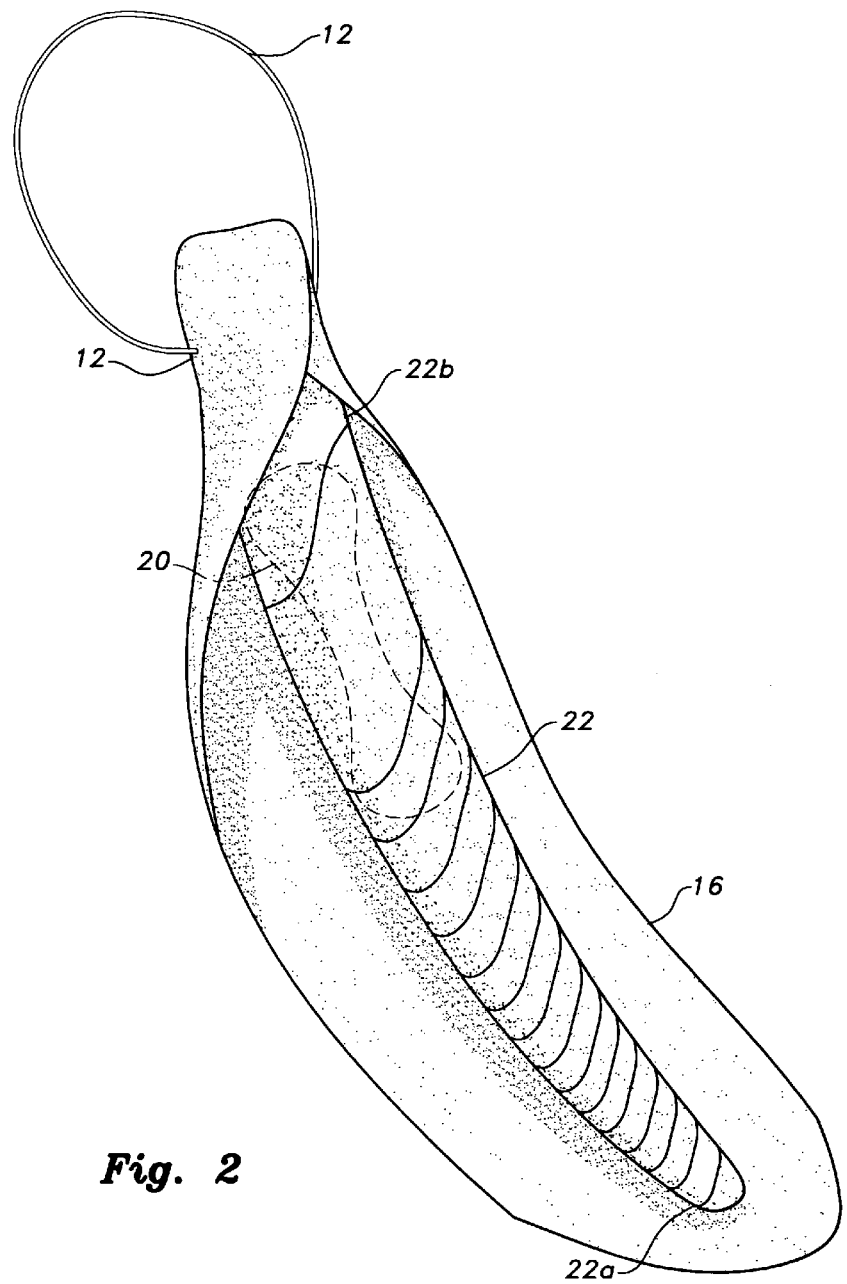
FIG. 2 is a perspective view of a sanitary napkin according to the present invention, broken away to show the inner core.
Figure 3:
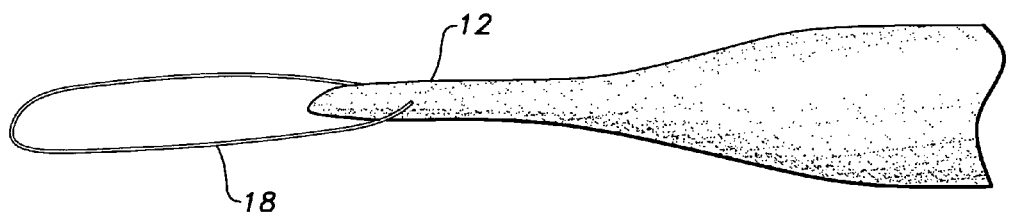
FIG. 3 is partial side view of a sanitary napkin according to the present invention.

Referring to FIGS. 1-3, the sanitary napkin 10 comprises an elongate member tapering in diameter from a wide, relatively flat first end 12 to a relatively cylindrical narrow end 14. The outer surface 16 of napkin 10 is fabricated from a soft, liquid permeable material to insure comfort. The first end 12 is provided with a positioning member in the form of a string 18 for purposes that will be explained below. An absorbent pad 20 (shown in phantom lines) is incased within the outer surface 16. As best seen in FIG. 2, outer surface 16 encapsulates a core member 22. Core member 22 is fabricated from a liquid absorbent material that is spirally or helically wound and tapers in diameter from a relatively large distal end 22$b$ to a relatively narrow proximate end 22$a$. As indicated above, end 12 is relatively flat, as best illustrated in FIG. 3.

In use, the napkin is positioned between the buttocks of a user (string member at rear). The buttocks act to hold the napkin in place. String member 18 aids in properly positioning the napkin. The configuration of the napkin 10 plus the use of undergarments function to retain the napkin in its proper position. The napkin 10 will absorb and retain therein any leakage from the vaginal (or rectal) area to prevent the staining discussed above. All parts are fabricated from biodegradable materials and the napkin can be attached to any sanitary pad. The napkin will be made in varied sizes.

It is to be understood that the present invention is not limited to the embodiment described above, but encompasses any and all embodiments within the scope of the following claims.

I claim:

1. An absorbent article used to absorb exudation or bodily fluids, comprising:
    an outer surface, the outer surface being fabricated from a liquid-pervious material;
    a core member having a longitudinal axis, a first end at one end of the axis, a second end at the opposite end of the axis, and an outer surface, the core member being fabricated from a liquid absorbent, biodegradable material, wherein the absorbent material is continuously spirally wound along the longitudinal axis from one end to the other so that the core member is tapered from the first end to the second end, the core member being encapsulated by the outer surface;
    and
    a positioning member attached to the first end of the outer surface.

2. The absorbent article according to claim 1, further comprising:
    a pad encased in the outer covering, the pad being fabricated from a liquid absorbent, biodegradable material.

3. The sanitary napkin according to claim 1, wherein the positioning member is a string.

4. The sanitary napkin according to claim 1, wherein the first end of the core member is flat and wide, and the second end is narrow.

* * * * *